United States Patent [19]

Alfano

[11] Patent Number: 5,042,494

[45] Date of Patent: Aug. 27, 1991

[54] METHOD AND APPARATUS FOR DETECTING CANCEROUS TISSUE USING LUMINESCENCE EXCITATION SPECTRA

[76] Inventor: Robert R. Alfano, 3777 Independence Ave., Bronx, N.Y. 10463

[21] Appl. No.: 449,510

[22] Filed: Dec. 4, 1989

Related U.S. Application Data

[60] Division of Ser. No. 245,081, Jun. 7, 1988, abandoned, which is a continuation-in-part of Ser. No. 186,747, Apr. 25, 1988, Pat. No. 4,930,516, which is a continuation of Ser. No. 796,859, Nov. 13, 1985, abandoned.

[51] Int. Cl.$^5$ .............................................. A61B 5/00
[52] U.S. Cl. ..................................... 128/665; 128/395
[58] Field of Search ............... 128/664, 665, 395, 398, 128/633; 606/3, 15, 16; 356/435

[56] References Cited

U.S. PATENT DOCUMENTS

| 4,648,892 | 3/1987 | Kittrell et al. | 128/634 |
| 4,768,513 | 9/1988 | Suzuki | 128/634 |
| 4,785,806 | 11/1988 | Deckelbaum | 128/303.1 |

OTHER PUBLICATIONS

Kittrell et al., "Diagnosis of Fibrous Arterial Atherosclerosis using Fluorescence" Applied Optics vol. 24, No. 15, Aug. 1985 pp. 2280–2281.
Spears et al., "Fluorescence of Experimental Atheromatous Plaques with Hematoporphyrin Derivative", J. Clin. Invest. vol. 71, Feb. 1983, pp. 395–399.

Primary Examiner—Ruth S. Smith
Attorney, Agent, or Firm—Irving M. Kriegsman

[57] ABSTRACT

A method and apparatus for detecting the presence of cancerous tissue using native visible luminescence. The tissue to be examined is excited with a beam of monochromatic light that causes the tissue to fluoresce over a spectrum of wavelengths. The intensity at which the excited tissue fluoresces can be measured either over a spectrum or at a predetermined number of preselected wavelengths. By determining the wavelength(s) at which maximum intensity(ies) are attained for the tissue in question and by comparing these peak wavelengths, either visually or electronically, to the peak wavelength(s) derived from a known non-cancerous tissue, or by comparing the luminescence spectrum of the excited tissue with the luminescence spectrum of a known noncancerous tissue and/or known cancerous tissue or the excitation spectra of the excited tissue with the excitation spectra of known cancerous and/or known non-cancerous tissue one can determine the carcinomatoid status of the tissue in question. Once it has been determined that the tissue is cancerous, it may by destroyed by ablation by exposing it to a beam of light from a high power laser. The invention is based on the discovery that the visible luminescence spectra for cancerous and non-cancerous tissue are substantially different and that the differences are such that visible luminescence from tissue can be used to detect the presence of cancer and also on the discovery spectral profiles of excitation spectra are similarly different.

6 Claims, 13 Drawing Sheets

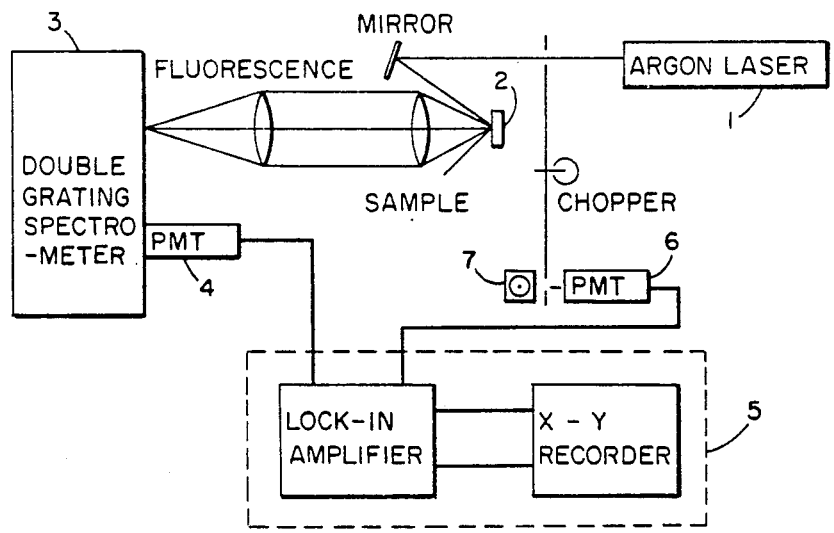
FIG. 1
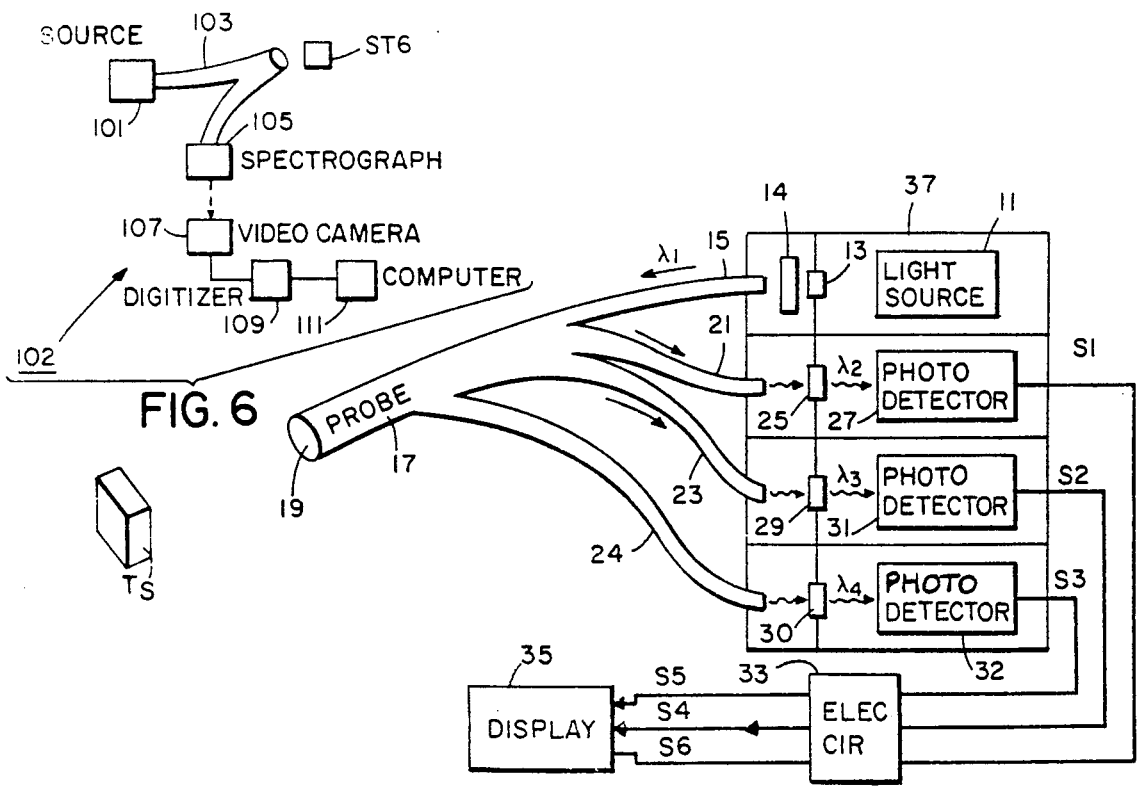
FIG. 6
FIG. 5

TABLE

THE RATIOS (R) BETWEEN THE INTENSITIES OF THE EXCITATION SPECTRA FROM TUMOR AND NORMAL BREAST TISSUES FOR EMISSION AT 520nm, 550nm, AND 600nm

| λ(nm)    | 352  | 396  | 457.9 | 473  | 488  | 514.5 |
|----------|------|------|-------|------|------|-------|
| R(520nm) | 0.79 | 4.30 | 5.38  | 3.42 | 2.59 | —     |
| R(550nm) | 0.85 | 3.86 | 5.16  | 4.47 | 3.53 | 1.56  |
| R(600nm) | 0.75 | 3.25 | 2.97  | 2.35 | 2.36 | 1.50  |

FIG. 16

METHOD AND APPARATUS FOR DETECTING CANCEROUS TISSUE USING LUMINESCENCE EXCITATION SPECTRA

This invention was made with Government support under Contract N00014-87-K-0431 awarded by the Department of the Navy. The Government has certain rights in this invention.

CROSS REFERENCE TO RELATED APPLICATION

This application is a division of application Ser. No. 245,081, filed 6-7-88 now abandoned. which is a continuation-in-part of U.S. Pat. application Ser. No. 186,747, filed Apr. 25, 1988 in the names of Robert R. Alfano and Michele A. Alfano now U.S. Pat. No. 4,930,516 which in turn is a continuation of U.S. patent application Ser. No. 796,859 filed on Nov. 13, 1985 in the names of Robert R. Alfano and Michele A. Alfano now abandoned.

BACKGROUND OF THE INVENTION

The present invention relates to a method and apparatus for detecting the presence of cancerous tissue and more particularly to a method and apparatus for detecting cancerous tissue using native visible luminescence.

Because a sufficiently effective method has not yet been developed to prevent cancer, cancer research has focused on the most effective ways to cure an organism that is diagnosed as having a cancer. As different as the various forms of treatment have been—ranging from excision to radiation to chemotherapy—all treatments have relied on one crucial step, detection of the cancerous tissue. The importance of detection cannot be stressed enough. Early detection not only indicates the presence of a cancer but also may give an indication as to where the cancer originated and as to what type of treatment will be the most safe and effective method. Early detection can provide such benefits because it reveals the state of maturation of the cancer cell. Cancer cells are clonal cells of a single "founder" cell that is the result of some mutation of the normal cell for the particular tissue. As a result of the mutation, the founder cell replicates and divides, eventually forming a mass of cells called a tumor. Tumors are harmful to an organism because they proliferate at a metabolic rate that exceeds that of the normal neighboring cells. As a result, the tumor grows at the expense of the normal neighboring tissue, ultimately destroying the normal tissue. One of the reasons why it is so difficult to completely cure an organism of cancer is that cancer cells have the ability to disseminate throughout the organism via lymphatic or circulatory systems and to create new tumors where they arrive. However, this ability to disseminate comes only to those cells that have lost the characteristic membrane glycoproteins of the mutated tissue. For this reason, it takes a while before cancer can spread. An advantage to early detection is that the cells can be examined for characteristic properties such as cell size and shape to determine the source of the cancer cells.

Clearly, the importance of an accurate technique that can be utilized in vivo or in vitro cannot be minimized. The advantage of an in vivo and in vitro technique is that sensitive tissue may be tested, relatively undisturbed, for example, with the use of an inserted optical fiber probe.

Presently, the diagnosis of cancer mainly relies on X-rays, nuclear magnetic resonance, nuclear radiation or invasive methods based on chemical laboratory analysis and biopsy. In view of the dangerous side effects of X-rays, nuclear radiation, and biopsies it appears that a definite need exists for a new technique for detecting cancer which can either eliminate or reduce the necessity of X-rays, nuclear radiation, and biopsies.

Although there exist many effective methods for detecting cancer, very few methods are based exclusively on the intrinsic properties of the cell and, as a result, interfere with normal tissues. For example, Hematoporphyrin derivative (HPD), which absorbs preferentially to cancerous tissue, is currently employed as a photosensitizer of tumors for photoradiation therapy. Unfortunately HPD interfers with normal tissue and does not make a good in vivo technique for detection. Flavins and porphyrin found in abundance for their effectiveness at transferring electrons in subcellular organelles known as mitochrondria are known to fluoresce in the visible light portion of the luminescence spectra.

Optical spectroscopy and laser technology offer new possible techniques for detection and characterization of physical and chemical changes which occur in diseased tissue, either invivo or invitro. This lends itself to a new approval for diagnosis of pathological changes in tissue.

The present invention is based, at least in part, on the discovery that the fluorescence spectra profile of cancerous tissue is different from the fluorescence spectra profile of normal tissue, the discovery that the fluorescence peak is blue-shifted (shifted to lower wavelengths) and in other samples red-shifted (shifted to longer wavelengths) in areas corresponding to flavin and porphyrin peaks and that the red peaks are reduced in intensity. Because this blue-shift (or red-shift) in the fluorescence spectra is an intrinsic property of the tissue, normal tissue is unaffected, making the monitoring of these fluorescence spectra an especially safe in vivo technique. A possible explanation for the blue-shift (or red-shift) and change in fluorescence spectral profile of cancerous tissue is that the flavins and porphyrins are in different environments that effect the fluorescence of these molecules. Flavins maybe blue-shifted (or red-shifted) when a protein closely associated to the flavin acquires net positive (blue-shift) or negative (red-shift) charge relative to its native state. Porphyrins, which fluoresce only in cancerous tissue are probably in the dissociated state since this is the only form that fluoresces. The abundance of free porphyrins in cancerous tissue may result from a reduction of the metal ion that serves to build the porphyrins in the proteins. Self absorption by hemoglobin molecules may cause the complex profile in normal tissue.

The discovery that certain biological molecules fluoresce differently in cancerous and non-cancerous tissue and that spectral changes in shape and shift to the blue (or red) for these molecules present a sufficient criteria for determination of cancerous tissue.

The present invention is also based in part of the discovery that the excitation spectra are different for normal and cancerous tissue.

In U.S. Pat. No. 2,437,916 to W. F. Greenwald there is described a technique for examining living tissue which involves illuminating the tissue with a beam of light and then measuring the intensity of the reflected light at certain wavelengths ranges using a phototube and different colored filters.

In U.S. Pat. No. 3,674,008 to C. C. Johnson there is described an instrument which quantitatively measures optical density of a transilluminated body portion. The instrument comprises a controllable, relatively low-frequency oscillator generating pulses which are applied to a light source through a first expand and delay circuit. A light-conducting source to one side of the body portion and a similar means optically couples another side of the body portion to a light detector. Alternatively, the light source and detector may be placed directly on the body portion. After compensation for ambient light, the output of the detector is coupled to a sample and hold circuit which is triggered by the controllable oscillator through a second expand and delay circuit. The stored signal in the sample and hold circuit is proportional to transmittance and calibrated display means. Methods of using the instrument in diagnosis are discussed, as are further applications to spectrophotometeric determinations.

In U.S. Pat. No. 3,963,019 to R. S. Quandt there is described a method and apparatus for detecting changes in body chemistry, for example, glycemia, in which a beam of light is projected into and through the aqueous humor of the patient's eye. An analyzer positioned to detect the beam on its exit from the patient's eye compares the effect the aqueous humor has on said beam against a norm. An excess or deficiency of glucose present in the aqueous humor produces a corresponding positive or negative variation in the exiting beam and thereby indicates a hyper or hypo glycemia condition in the body chemistry of the patent being tested.

In U.S. Pat. No. 4,029,085 to D. P DeWitt et al there is described a method for determining the bilirubin concentration in the blood serum of a person from measurement of the spectral reflectance of the skin. The disclosed method detects the severity of jaundice, common neonatal condition, and enables determination of the type of treatment regimen needed to prevent the billirubin level from becoming sufficiently high to cause kernicterus which can result in brain damage. The method includes measuring the reflectance of the skin within a predetermined frequency spectrum, and more particularly, at a number of specific wavelengths in the visible portion of the spectrum.

In U.S. Pat. No. 4,290,433 to Robert R. Alfano there is described a method and apparatus for detecting the presence of caries in human teeth using visible luminescence. A region to be examined is excited with a beam of monochromatic light. The intensity of the visible light emitted from the region is measured at two predetermined wavelengths, one where the intensity dependence of the spectra is about the same for caries and non caries and the other where the relative intensity changes significantly in the presence of caries. A signal corresponding to the difference in the two intensities is obtained and then displayed. By first determining the magnitude of the difference signal at a nondecayed region, any increases in the magnitude as other regions are probed on the discovery that the visible luminescence spectra for decayed and nondecayed regions of a human tooth are substantially different and that the differences are such that visible luminescence from teeth can be used to detect the presence of caries.

In *Medical and Biological Engineering*, Vol 6, No 4 August, 1968, pp. 409-413 there is described a technique for tissue identification during needle puncture by reflection spectrophotometry.

SUMMARY OF THE INVENTION

It is an object of this invention to provide a new, rapid, and improved technique for detecting the presence of cancerous tissue.

It is another object of the invention to provide a technique for detecting the presence of cancerous tissue which does not involve the use of X-rays.

It is still another object of this invention to provide a technique for detecting the presence of cancerous tissue that does not involve the use of other potentially harmful radiation, such as ultraviolet radiation or nuclear radiation.

It is yet still another object of this invention to provide a technique for detecting the presence of cancerous tissue of a person which is reliable, rapid, inexpensive and easy to use.

It is another object of this invention to provide a technique for detecting the presence of cancerous tissue which does not require the use of X-ray sensitive plates or film.

It is yet still another object of this invention to provide a technique for detecting the presence of cancerous tissue using visible light as an exciting source and native visible luminescence to probe for the cancerous tissue.

It is still another object of this invention to provide a technique for detecting the presence of cancerous tissue using excitation spectra to distinguish cancerous from normal tissue;

It is still another object of this invention to provide a new diagnostic tool for the pathologist to evaluate a biopsy in cancer and for a surgeon to evaluate if all cancerous tissue has been removed, using fluorescence spectroscopy.

It is a further object of this invention to provide a new diagnostic tool for the pathologist to evaluate a biopsy in cancer and for a surgeon to evaluate if all cancerous tissue has been removed, using fluorescence spectroscopy using excitation spectroscopy.

It is still another object of this invention to provide a in-vivo spectroscopy diagnosis technique using an optical fiber (endoscopy) to determine cancer inside a body (i.e. stomach, lungs, urinary tract, intestinal tract, brain, colon, eye and throat).

It is still another object of this invention to provide a in-vitro spectroscopy diagnostic technique for a pathologist to test biopsy samples.

It is another object of this invention to provide a technique for detecting and then destroying cancerous tissue.

It is a further object of this invention to provide a new and improved technique for determining if tissue is cancerous or normal.

The present invention is based on the discovery that the shape of the native visible luminescence spectra from normal and cancerous tissue are substantially different, and in particular, that for cancerous tissue there is a shift to the blue (or red) with different intensity peaks and also on the discovery that the excitation spectra for native normal tissue and cancerous tissue are different.

The method for detecting the presence of cancerous tissue involves, according to one embodiment of the invention, illuminating a region to be examined with a beam of monochromatic light, and then determining if the resulting luminescence spectrum more closely represents the luminescence spectrum for a cancerous tissue than the luminescence spectrum for a normal tissue. The determining can be achieved by comparing the resulting luminescence spectrum either (1) with a luminescence spectrum for normal tissue and observing how it differs or (2) with a luminescence spectrum for cancerous tissue and observing how it differs or (3) with a luminescence spectrum for cancerous tissue and with a luminescence spectrum for normal tissue and observing which of the two spectra it more closely represents. In another embodiment excitation spectra are compared, rather than luminescence spectra the excitation spectra being obtained by varying the excitation wavelength and then detecting the intensity at a preselected wavelength where luminescence occurs.

The apparatus for detecting the presence of cancerous tissue according to one embodiment of the invention includes a monochromatic light source, a spectrograph, a fiber optics (endoscope) a video camera, a digitizer, a computer and a display.

The apparatus for detecting the presence of cancerous tissue according to another embodiment of the invention includes a monochromatic light source whose wavelength is variable, a spectrometer, and a light detector.

In still another feature of the invention, a high power laser is provided for destroying the cancerous tissue by ablation, after it has been detected.

The foregoing and other objects and advantages will appear from the description to follow. In the description, reference is made to the accompanying drawing which forms a part thereof, and in which is shown by way of illustration specific embodiments for practicing the invention. These embodiments will be described in sufficient detail to enable those skilled in the art to practice the invention, and it is to be understood that other embodiments may be utilized and that structural changes may be made without departing from the scope of the invention. The following detailed description is therefore, not to be taken in a limiting sense, and the scope of the present invention is best defined by the appended claims.

BRIEF DESCRIPTION OF THE DRAWINGS

FIG. 1 is a schematic diagram of an experimental setup used to measure luminescence spectra from various tissues;

FIG. 5 is a simplified diagram of one embodiment of an apparatus of the invention;

FIG. 6 is a simplified diagram of another embodiment of the invention;

FIG. 16 is a table showing the ratios (R) between the intensities of the excitation spectra from tumor and normal breast tissues for emission at 520 nm, 550 nm and 600 nm.

DETAILED DESCRIPTION

Figure 2A:
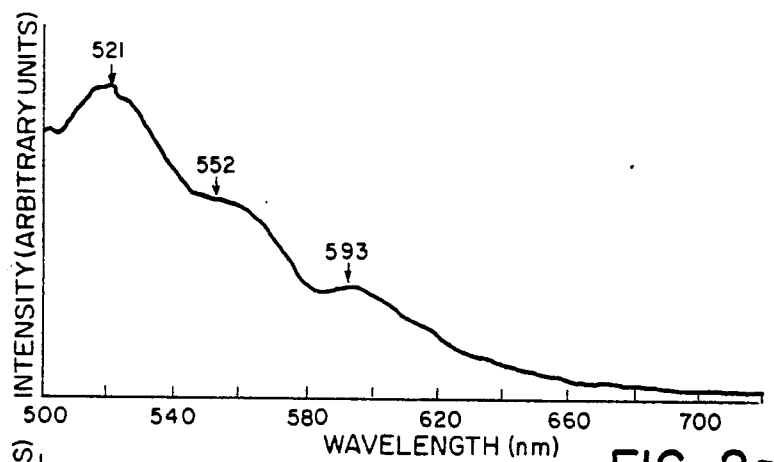
FIGS. 2(a) and 2(b) are fluorescence spectrum of rat prostrate tumor and normal rat prostrate, respectively.

As used herein, the term "tumor" means cancerous.

The present invention is directed to a method and apparatus for detecting the presence of cancerous tissue using native visible luminescence.

An experimental arrangement used to measure the luminescence spectra from the various tissues is shown in FIG. 1. A 10 mw Argon ion laser 1 operating a 488 nm was focused on the front surface of the tissue 2 to a spot size of about 100 $\mu$m. The native luminescence from the front surface was collected into a double SPEX-1/2 m grating scanning spectrometer 3 blazed at 500 nm. A photomultiplier tube (PMT) RCA 7265 (S-20) 4 located at the exit slit of the spectrometer 3 measured the intensity at different wavelengths. The spectral bandwidth was 1.8 nm. The output of the PMT was connected to a Princeton Applied Research lock-in recorder combination 5 to display the spectrum. Both the laser and reference signal from light 7 and detected by a PMT 6 were chopped at 200 Hz. The spectra were not corrected for the spectrum response of the system. Each sample emission spectrum was run three times for reproducibility. The measured spectra were stable in time and different regions yielded similar spectra.

The luminescence emitted from cancerous and normal tissues from rat prostate and kidney were investigated. The spectra from a rat female bladder tumor and a mouse bladder tumor were also measured. All tumors were subcutaneously implanted. Rat prostate tumors were implanted in Fischer/Copenhagen male ($f_1$) rats and were five weeks old at the time of the testing. Rat kidney tumors were implanted in Wistor/Lewis rats and were four weeks old. Rat bladder tumor was implanted in a female Fischer rat and was four weeks old at the time of testing. Mouse bladder tumor was implanted in a female C3HHe mouse and was also four weeks old. All tissue samples were nonnectrotic, clean free and approximately 1 gm in weight. All tissue samples were solid chunks but not cut to any particular specificity, and were few millimeters thick. Each tissue sample was placed in a clean pyrex test tube for these luminescence studies.

Figure 2B:
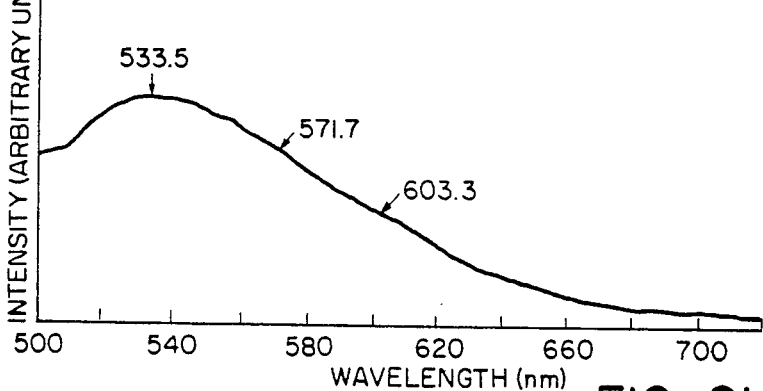

The spectral curves for the cancerous and normal tissues are displayed in FIGS. 2-4. One notices the differences in the spectra between the normal and cancerous tissues. The prominent maxima in the spectra from rat prostate tumor [FIG. 2(a)] and rat normal prostate [FIG. 2(b)] are located at 521 and 533.5 nm., respectively. The prostate tumor spectrum has two subsidiary maxims located at 552 and 593 nm while no additional maxima are recorded in the normal prostate spectrum. In the prostate tumor spectrum there are four points of inflections located at 538.3, 571.7, 587.0, and 619.5 nm. On the decreasing side of the normal prostate curve there are two points of inflection located at 571.7 and 603.3 nm, as shown in FIG. 2(b).

Figure 3A:
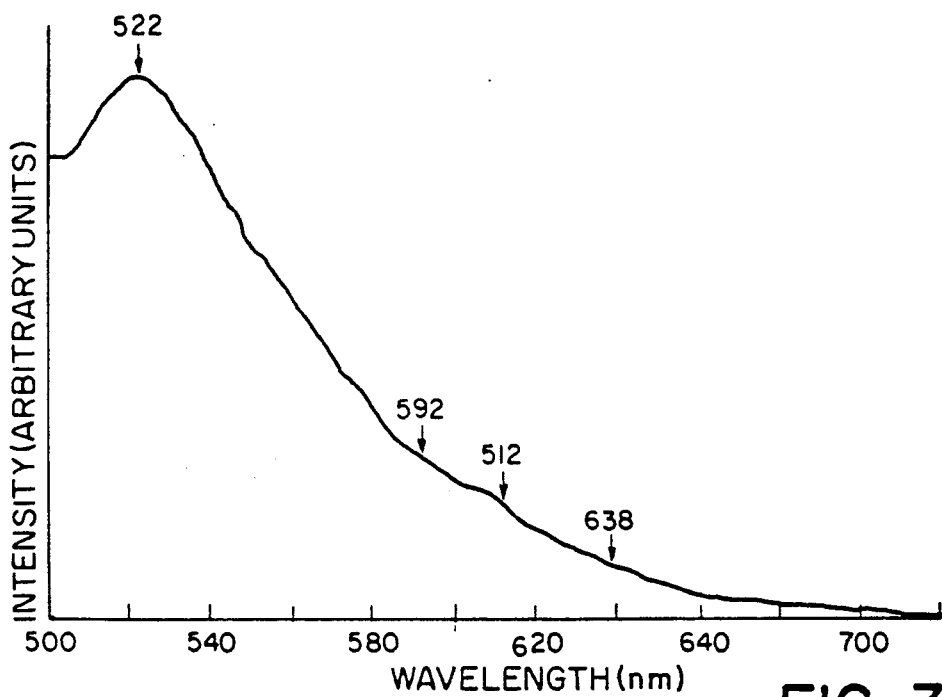
FIGS. 3(a) and 3(b) are fluorescence spectrum of rat kidney tumor and normal rat kidney, respectively.
Figure 3B:
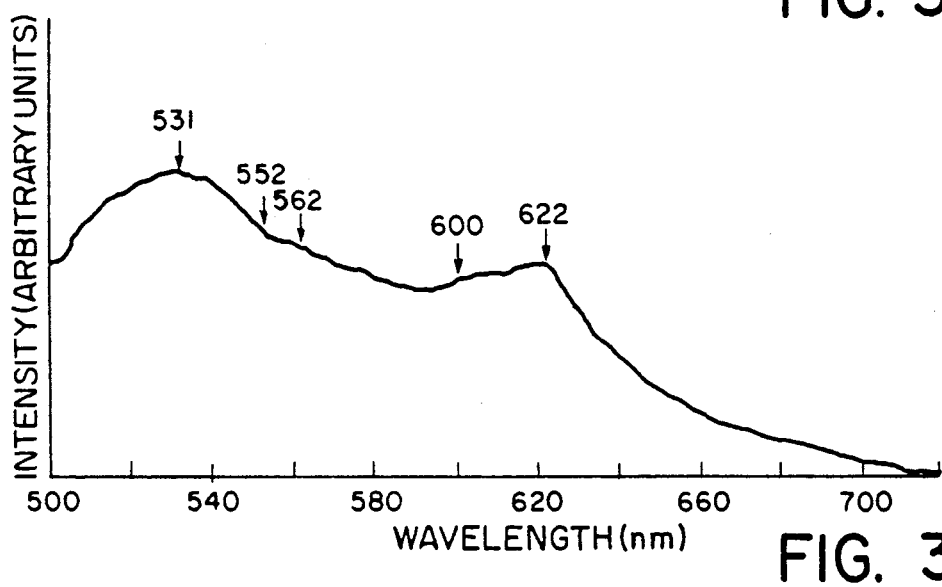

The main maxima in the spectra from male rat kidney tumor [FIG. 3(a)] and normal male rat kidney [FIG. 3(b)] are also located at 522.0 and 530.6 nm., respectively. After the first prominent peak, the spectrum from the rat kidney tumor decreases monotonically and there are three small peaks located at 592, 612, and 638 nm. Along this declining side of the curve there are four inflectionary points located at 548.7, 559.3, 581.3, and 604.2 nm. However, after the first prominent peak for the normal male kidney, the spectrum declines monotonically until it reaches a wavelength at 590.8 nm where it starts to increase. Along the declined portion of the curve there are three smaller peaks located at 562, 600 and 622 nm. The spectrum also contains three inflectionary points located at 522 and 595 nm. Similar spectral differences have been observed in human tissues of the lung and breast.

Figure 4A:
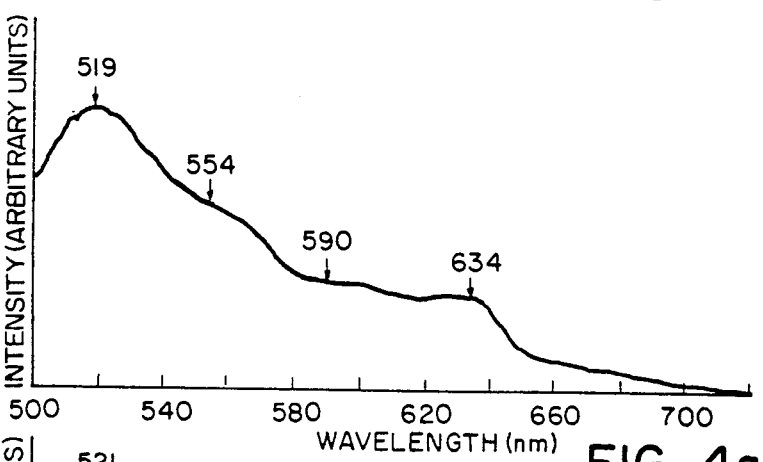
FIGS. 4(a) and 4(b) are fluorescence spectrum of rat bladder tumor and mouse bladder tumor.

The salient features of the rat bladder tumor spectrum are its four peaks. [FIG. 4(a)]. The first prominent peak is located at 519.1 nm; other smaller peaks are located at 554, 590, and 634 nm. The spectrum also contains two inflectionary points locate at 567.0 and 605.2 nm. After the minimum at 614.7 nm the curve starts rising to the last peak at 634.0 nm, after which there is a fall off to zero intensity.

Figure 4B:
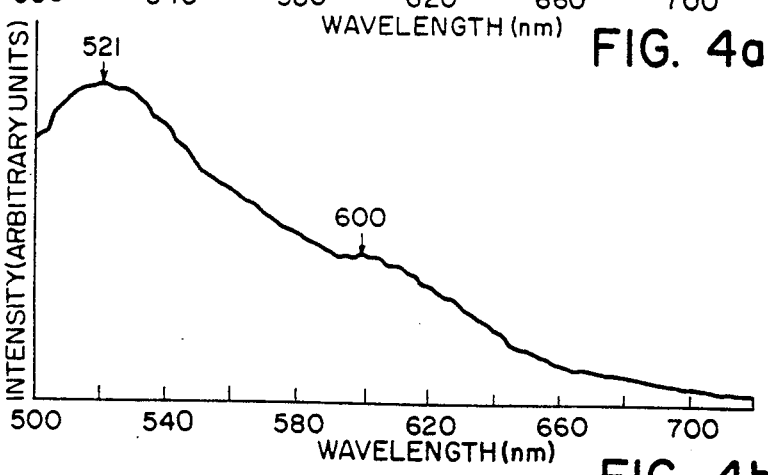

The salient features of the mouses bladder tumor spectrum are its two wide peaks [see FIG. 4(b)]. The first prominent peak is located at 521.0 nm, and the other at 600.0 nm. The spectrum starts declining from 610 to 648 nm after which its slope changes and decays slowly to zero. There are two points of inflection in the spectrum, one located at 559.2 nm and the other at 648.2 nm.

The summary of the results from the fluorescence measurements shows the following salient features that are found in common among the tumor spectra:

1. Location of the prominent maxima of the tumor spectra all occur at about 521.0 nm.
2. The width of the prominent maxima are virtually the same, approximately spanning 1.5 nm.
3. Secondary peaks which are in common to all tumors occur between 590-640 nm.
4. The secondary peak which is also in common with the rat prostate tumor and the rat bladder tumor is in the range of 552-554 nm.
5. The secondary peak which is also in common with the rat kidney tumor and the rat bladder tumor fall in the range of 634-638 nm.

Upon analysis of the data between the two normal spectra, one recognizes the prominent maxima are located at 530-533 nm and the width of the prominent maxima are broad, each spanning 38 nm.

The most salient differences between the cancerous and the normal tissues are that the spectral profiles are very different and that the cancerous prominent maxima are shifted and located around 521 nm, whereas the prominent maxima of the normal tissues spectra are located at about 531 nm.

As can be seen, when protein containing fluorphors either gain positive charge ions or lose negative charge ions the fluorescence from the fluorphors have been noted to be blue shifted. The prominent maxima of all cancerous spectra exhibit in our results a 10 nm blue shift, suggesting an accumulation of positive ions, or a depletion of negative (or positive) ions in the mitochrondria of cancerous cells, thus causing the flavins to emit at 521 nm instead of 531 nm.

The emission from 590-640 nm is attributed to porphyrins. In cancerous tissue the relative intensity of porphyrins bands are different, usually smaller in intensity from its normal counterpart. The spectral changes can be caused by other species such as hemoglobin. Similar differences have been observed in human lung and breast tissues.

Referring now to FIG. 5. there is illustrated an embodiment of an apparatus for detecting cancerous tissue according to the teachings of this invention.

The apparatus includes a source 11 of white light, such as a tungsten-halogen filament lamp, and a narrow band filter 13. Alternatively, source 11 may comprise a laser. Light source 11 has power coupled to it from a conventional power supply (not shown). Narrow band filter 13 has a bandwidth of less than about 30 nm and preferably less than about 10 nm and is designed to pass light at a wavelength $\lambda_1$.

Light from source 11 that is passed by filter 13 is passed through a chopper 14 which removes any ambient light present and is then fed into an input leg 15 of a fiber optic probe 17. The light entering fiber optic probe 17 emerges at the probing end 19 and impinges on tissue Ts to be tested. Light from tissue Ts enters probing end 19 and is conducted out of fiber optic probe 17 through output legs 21, 23, and 24, which are located at the same end as input leg. 15.

Alternatively, the light from tissue Ts can be imaged into a spectrograph or optical filters coupled to a video silicon intensified target camera computer for displaying the entire spectra. The light can be collected and imaged using a lens or a fiber optic bundle into a video camera.

Fiber optic probe 17 is made up basically of a bundle of optical fibers. The diameter of the bundle is preferably about ½ to 5 nm. The fibers within the bundle are preferably randomly arranged to reduce any geometrical collection effects. Fiber optic probe 17 may include a lens or lens system (not shown) at the probing end 19 so that non-contact probing may be achieved.

Light emerging from output leg 21 is passed through a narrow band filter 25 having a bandwidth of less than about 10 nm, and designed to pass light at a wavelength $\lambda_2$, and impinges on a photodetector 27. Light emerging from output leg 23 is passed through a narrow band filter 29 having a bandwidth of less than about 10 nm and designed to pass light at a wavelength $\lambda_3$, and impinges on photodetector 31. Light emerging from output leg 24 is passed through narrow band filter 30 having a bandwidth of less than 10 nm and designed to pass light of wave-length $\lambda_4$ and impinges on photodetector 32.

The value of $\lambda_1$ is between 350 and 500 nanometers. Photodetectors 27, 31 and 32 are conventional photodetectors having maximum sensitivity in the regions of interest, namely at wavelengths $\lambda_2$ and $\lambda_3$ and $\lambda_4$ respectively of the fluorescence spectra.

Figure 7:
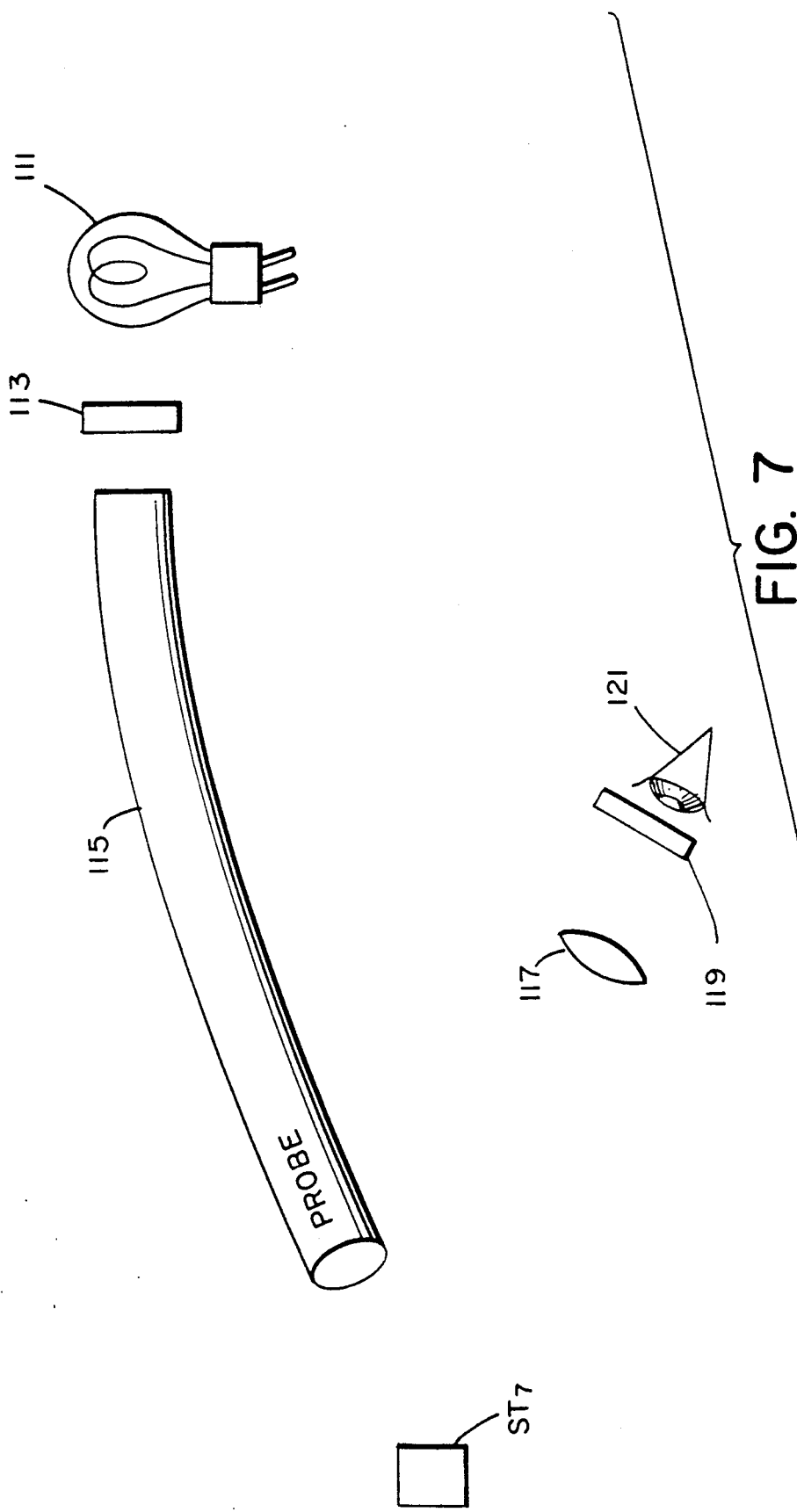
FIG. 7 is a simplified diagram of another embodiment of an apparatus of the invention.

The wavelengths are chosen where the largest difference in intensity occurs for cancerous and normal tissues, i.e. $\lambda_2 = 531$ nm, $\lambda_3 = 522$ nm, $\lambda_4 = 633$ nm. By using more detectors at more wavelengths one can more accurately determine differences in the spectra. Comparing the entire spectra using video spectroscopy such as shown in FIG. 7 results in a more accurate way to find cancer.

Photodetectors 27, 31 and 32 each produce an electrical signal output whose magnitude S1, S2 and S3 respectively, is proportional to the intensity of the incident light. The electrical output signals from photodetectors 27, 31 and 32 are each fed into an electronic circuit 33 which produces three output signals S4, S5 and S6, one corresponding to the ratio of S1 and S3 and the third corresponding to the ratio of S2 to S3, another corresponding to the ratio of S1 and S2. The three output signals are fed into a display where they are displayed 34. The difference in the signals (i.e. the difference between signals S1 and S2 or S2 and S3) could also be used and compared.

Light source 11, narrow band filters 13, 25, 29 and 30 and photodetectors 27, 31 and 32 are preferably all situated in a light-tight compartmented housing 37.

In detecting the presence of cancerous tissue in accordance with this embodiment of the invention, the ratios of the three probe signals S1, S2 and S3 are first determined for a known noncancerous region for the particular organ containing the tissue under test. Any changes in the ratios between signals S1 and S2 and S3 will indicate that the tissue is cancerous.

Instead of taking the ratios between signals S1 and S2 and S3, the differences or ratios of any two as opposed to three signals, such as S1 and S2 may be used to determine the relative change of the spectra. This may be achieved using any conventional type of difference circuit for differences or a divider circuit for ratios.

Referring now to FIG. 6, there is illustrated a simplified diagram of another embodiment 102 of the invention. Monochromatic light from a source 101 is transmitted by a fiber optic probe 103 for a sample tissue ST6 to be tested. Light from the sample tissue ST6 is transmitted by fiber optic probe 103 to a spectrograph (i.e. dual zero dispersion) 105 constructed so as to detect native luminescence emitted light from the sample tissue ST6. The output of the spectrograph 105 is imaged by a video camera 107 whose output is fed through a digitizer 109 into a computer 111. The spectrum of emitted light along with a spectrum of emitted light for a normal tissue (for the particular organ in question) are both displayed on a display (such as a TV monitor). The difference in spectra is obtained by a computer and then displayed to determine if the tissue is cancerous.

In FIG. 7 there is shown another embodiment 110 of the invention. Light from a source 111 is passed through a narrow band filter 113 where it is transmitted by a fiber optic probe 115 to the tissue ST7 to be tested. Native luminescence emitted from tissue ST7 is imaged by a lens 117 through a filter wheel 119 having two or more filters where it is imaged on the eye 121. Instead of a filter wheel and eye, the light from lens 117 may be imaged onto the slit of a spectrograph (i.e. dual zero dispersion) and then processed as in the FIG. 6 embodiment.

Figure 8:
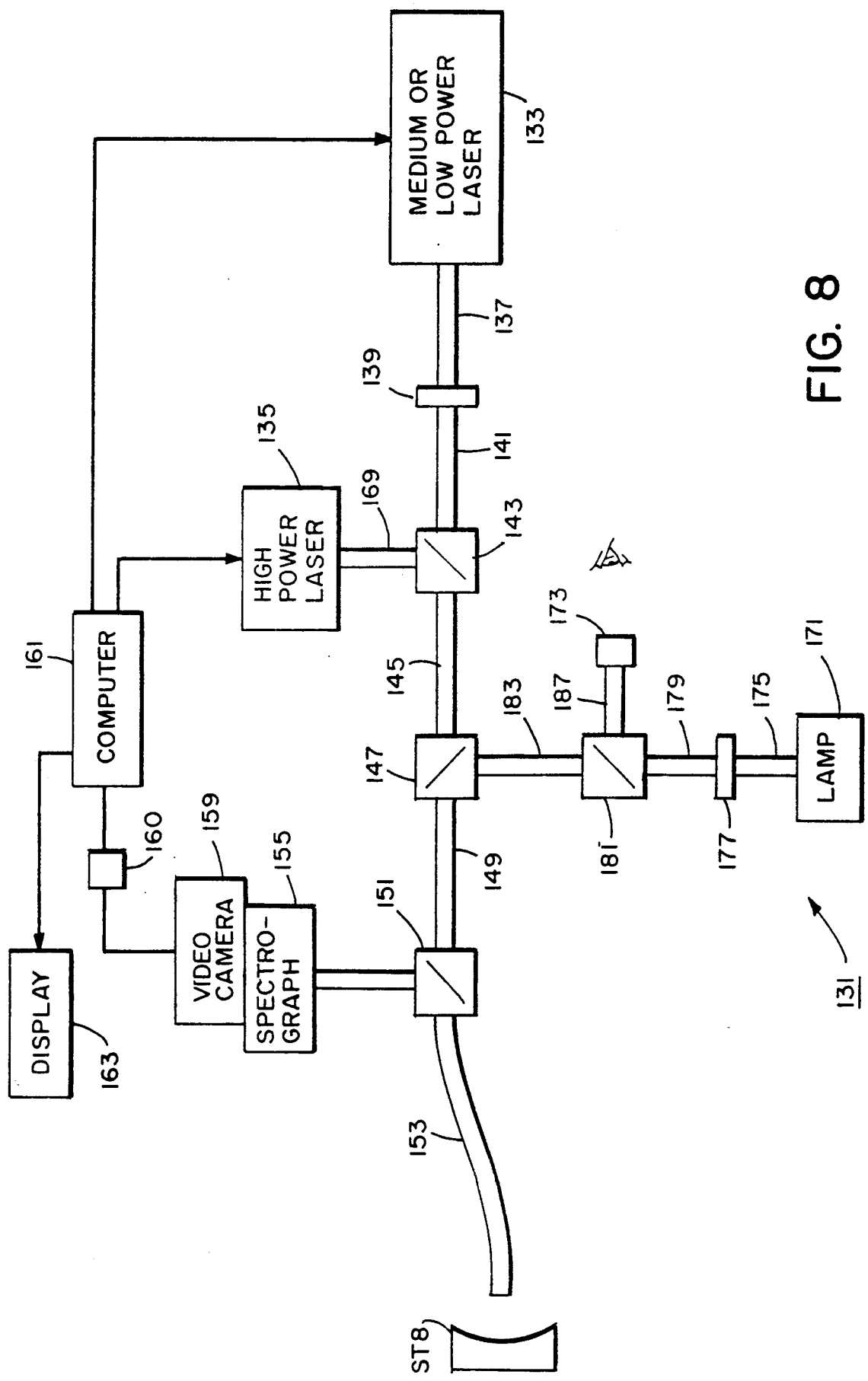
FIG. 8 is a simplified diagram of still another embodiment of an apparatus of the invention.

In FIG. 8 there is shown another apparatus constructed according to this invention, the apparatus being identified by reference numeral 131. Apparatus 131 includes a first laser 133 whose output beam is used to detect the cancerous tissue and a second laser 135 whose output beam is used to destroy the cancerous tissue after it has been detected as will hereinafter be described. Laser 133 is a low or medium power laser such as an argon laser or a helium-cadmium laser. Laser 135 is a high power laser such as a Q-switched laser, a copper vapor laser, a gold vapor laser, a nitrogen laser or a dye laser.

Light from laser 133 is transmitted by an optical fiber bundle 137 to a filter 139 which filters out all light but the preselected wavelength. Light passed by filter 139 is transmitted by an optical fiber bundle 141 to a dichroic coupler 143 which is designed to transmit light from laser 133 and reflect light from laser 135. Light transmitted through coupler 143 from laser 133 is transmitted by an optical fiber bundle 145 to a beamsplitting coupler 147. Light transmitted through coupler 147 from coupler 143 is transmitted by an optical fiber bundle 149 to a beam splitting coupler 151. Light transmitted through beamsplitting coupler 151 is transmitted by an optical fiber bundle 153 which functions as an endoscope and strikes sample tissue ST8 which is being examined.

Light subsequently emitted from sample ST8 (i.e. the native luminescent radiation) and striking bundle 153 is transmitted back to beamsplitting coupler 151 where it is reflected to an optical fiber bundle 155 which transmits the light to a spectrograph 157. The output of spectrograph 157 is imaged by a video camera 159. The output of video camera 159 is fed through a digitizer 160 into a computer 161 where it is compared with a spectrum of emitted light for a normal tissue to see if the tissue is cancerous.

The results obtained in computer 161 (i.e. the difference in spectra) are displayed in a display 163. If the results are positive, computer 161 sends a signal to activate laser 135. Light from laser 135 is transmitted through fiber bundle 169 to coupler 143 and is then reflected by coupler 143 through bundle 145, coupler 147, bundle 149, coupler 151 and endoscope 153 where it strikes sample ST8 and destroys the cancerous tissue by ablation.

A vacuum pump (not shown) can be used to draw out the cancerous tissue fragments.

Apparatus 131 also includes a lamp 171 for illuminating the area being examined (or treated) at an appropriate time, so that it can be visually observed through an eyepiece 173 by a person such as a doctor. Light from lamp 171 is fed into coupler 147 through a fiber bundle 175, a filter 177, a fiber bundle 179, a beamsplitter 181 and a fiber bundle 183. From coupler 147 the light is fed into endoscope 153. The illuminated area is viewed through eyepiece 173 which is coupled to beamsplitter 181 through optical fiber bundle 187.

Instead of comparing the spectrum obtained with a spectrum for normal tissue the spectrum could be compared with a spectrum for known cancerous tissue and the differences displayed.

Also, instead of simply displaying differences, the spectra themselves can be displayed and the decision made by the viewer as to whether it is cancerous.

In another arrangement the spectrum obtained is compared with spectra for normal and for cancerous tissue and a determination made as to which of the two spectra the sample spectrum more closely represents.

In another embodiment of the invention, excitation spectra are generated and used for detecting the presence of cancerous tissue in a similar manner as the luminescence spectra. The excitation spectra are obtained by measuring the intensity of the native luminescence at a preselected emission wavelength as the excitation wavelength is varied.

Excitation spectroscopy provides information on which bands are responsible for the observed spectroscopic differences. Experimental results have shown that the differences in the excitation spectra for the normal and cancerous tissues are pronounced.

Figure 9:
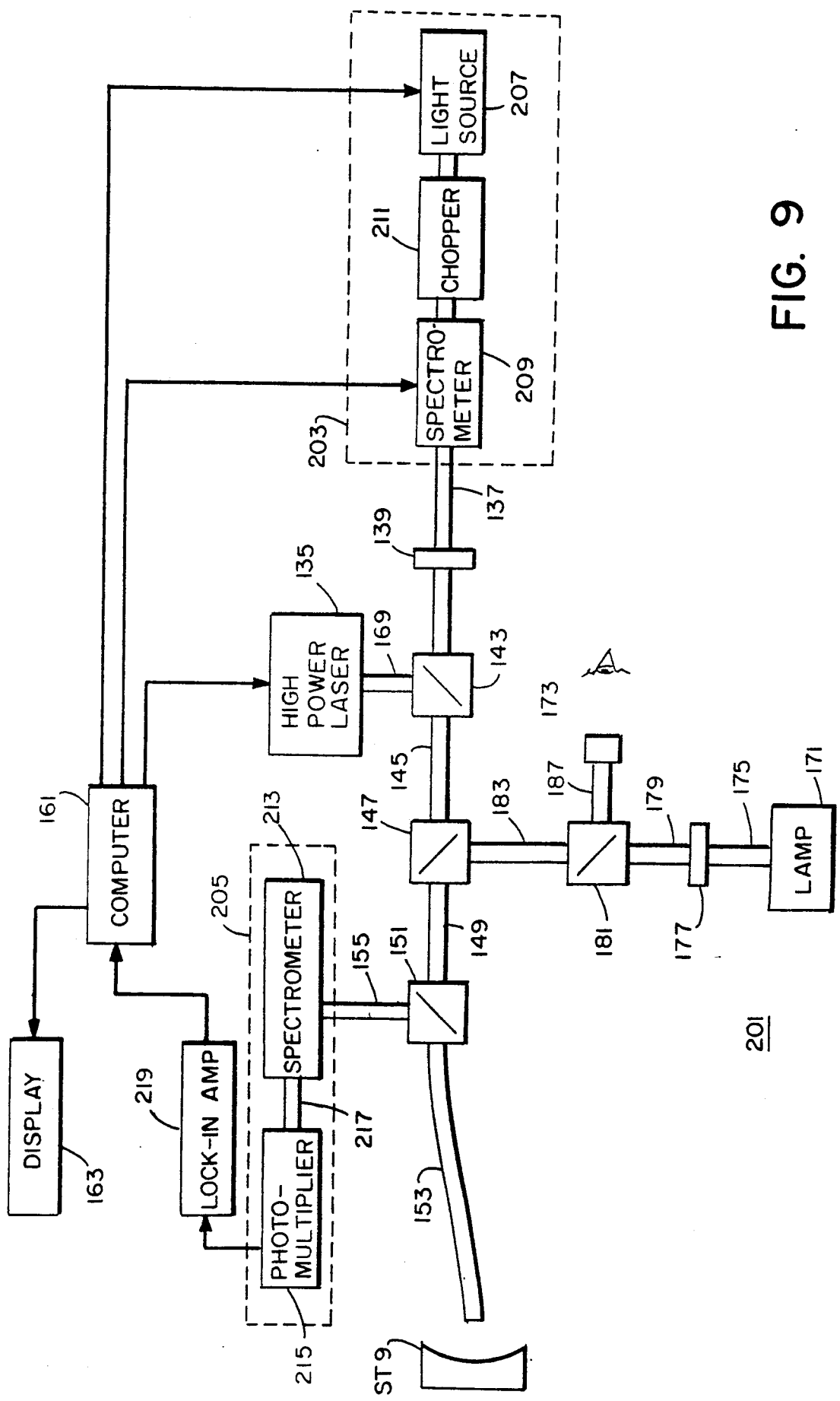
FIG. 9 is a simplified diagram of still another embodiment of an apparatus of the invention.

An apparatus 201 for obtaining excitation spectra and also for destroying the tissue examined if desired if it is cancerous is shown in FIG. 9. The apparatus includes means 203 for illuminating a sample ST9 with a beam of monochromatic light whose wavelength is varied and means 205 for measuring the intensity of emitted light at a preselected wavelength. Apparatus 201 is similar to apparatus 131, the differences being that laser 133 is replaced by a light source 207, a spectrometer 209 and a chopper 211 and the spectrograph 157 and video camera 158 are replaced by a spectrometer 213, a photodetector such as a photomultipler tube 215, an optical fiber bundle 217 and a lock-in amplifier 219. Light source 207 is a source of white light and may be for example a tungsten-halogen lamp. In using apparatus 201, light from source 207 is chopped and fed into spectrometer 209. The output of spectrometer 209 is transmitted through the various beamsplitters and optical fiber bundles and strikes sample ST9. The wavelength of the output of spectrometer 209 is varied by turning a knob (not shown) or scanning with a motor in spectrometer 209. The intensity of the emitted light is fed into spectrometer 213 whose output is detected by detector 215. The output of detector 215 is fed into lock-in amplifier 219 whose output is fed into computer 161. The excitation spectra so obtained is then compared with excitation spectra for normal and/or cancerous tissue and a determination made if the tissue is cancerous based on the comparison. Instead of a lock-in amplifier 219, a dc meter could be employed. The light emitted from spectrometer 209 is monochromatic and varied over a range of wavelengths. Accordingly, means 205 measures the intensity of emitted light at a preselected wavelength as the excitation wavelength is varied. Laser 135 is used to destroy to tissue if it is deemed desirable.

Spectrometer 213 can be replaced by an appropriate filter, if desired.

Experimental apparatus used to obtain excitation spectra from a sample native human breast tissues was a Perkin-Elmer LS-5 Fluorescence Spectrometer. Frontal excitation was used to pump the tissue samples. The excitation spectra were scanned from 300 nm to 500 nm for an emission peak at 520 nm, from 300 nm to 530 nm for an emission peak at 550 nm and from 300 nm to 580 nm for an emission peak at 600 nm. The emission peaks were chosen to be 520 nm, 550 nm, and 600 nm because these peaks are prominent in the emission spectra of the native breast tissues.

The tissue samples were put in plastic square cells which did not generate strong background in the excitation spectrum region from 300 nm to 580 nm after ND filters were placed in the emission spectrum path to reduce emission. Three pairs of human breast normal and tumor (cancerous) tissues were measured. The excitation spectrum profiles were consistent with each other.

Typical excitation spectra from native normal and tumor (cancerous) human breast tissues emitted at 520 nm, 550 nm, and 600 nm are shown in FIGS. 10 through 15. One notices that the excitation spectrum profiles are quite different from the normal and tumor tissues.

The excitation spectra consists of two wide bands, centered in the ultraviolet (uv) and visible. The uv band of the excitation spectra for the normal breast tissues in FIG. 10 and FIG. 12 consist of three sharp peaks located at 336 nm, 352 nm, and 371 nm. The major peak is centered at 352 nm. However, there are no clear sharp peaks in the uv bands of the excitation spectra of cancer tissues. In FIG. 11 and FIG. 13 a very small peak at 352 nm can be observed. The cancer spectra are broader with a characteristic feature existing at 396 nm.

Figure 10:
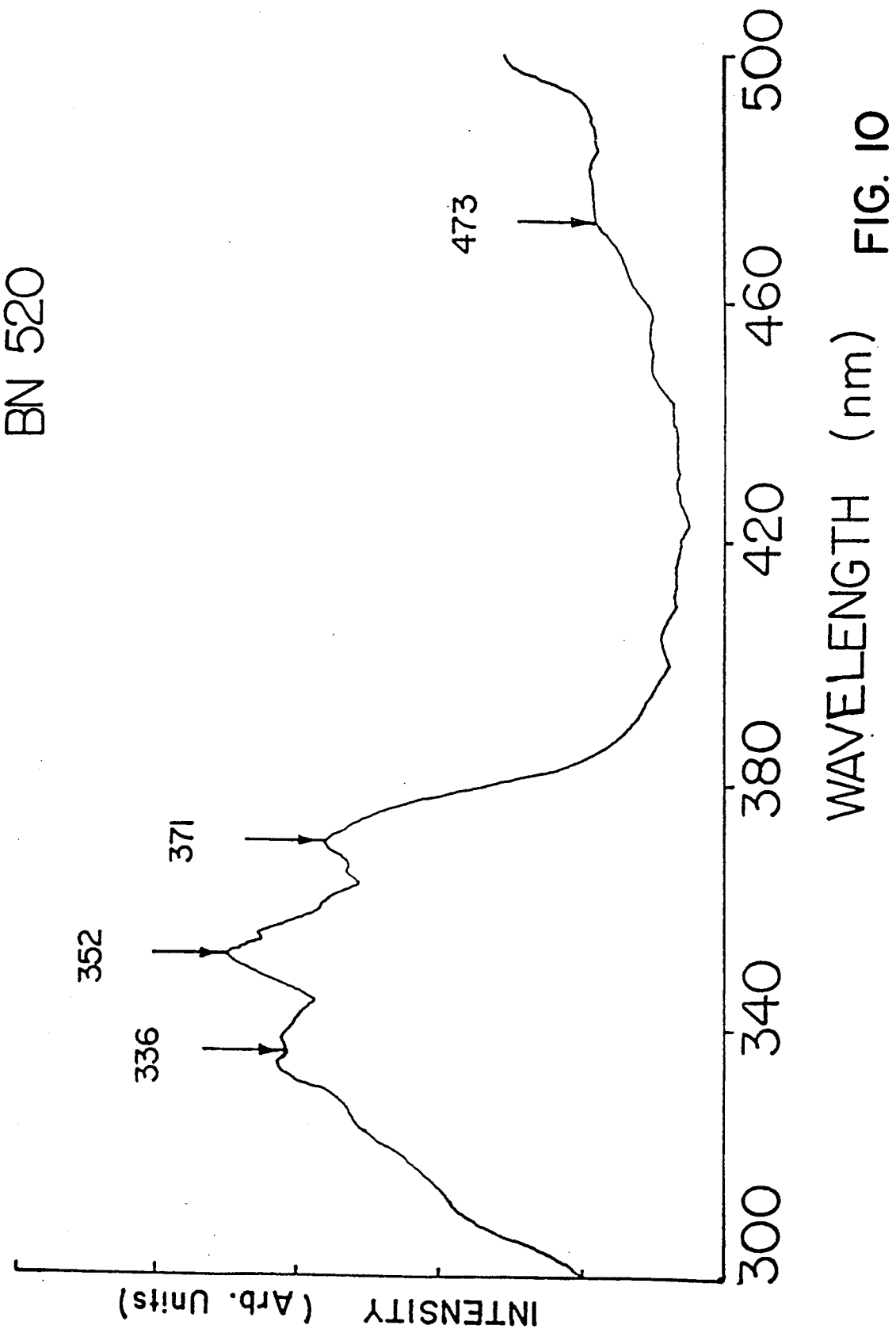
FIGS. 10 and 11 are typical excitation spectra measured at 520 nm from native human breast normal tissue and native human breast tumor tissue.
Figure 11:
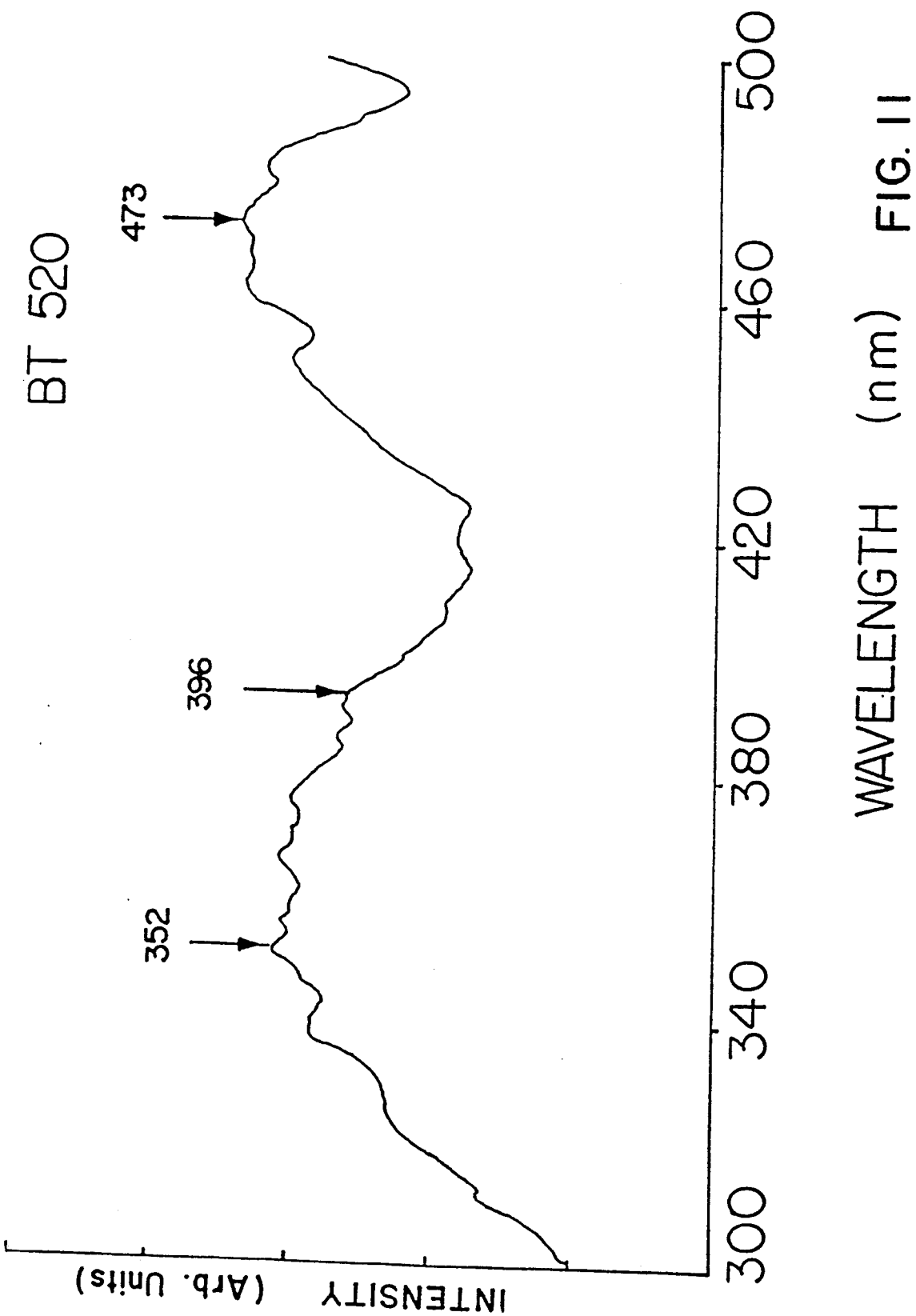
Figure 12:
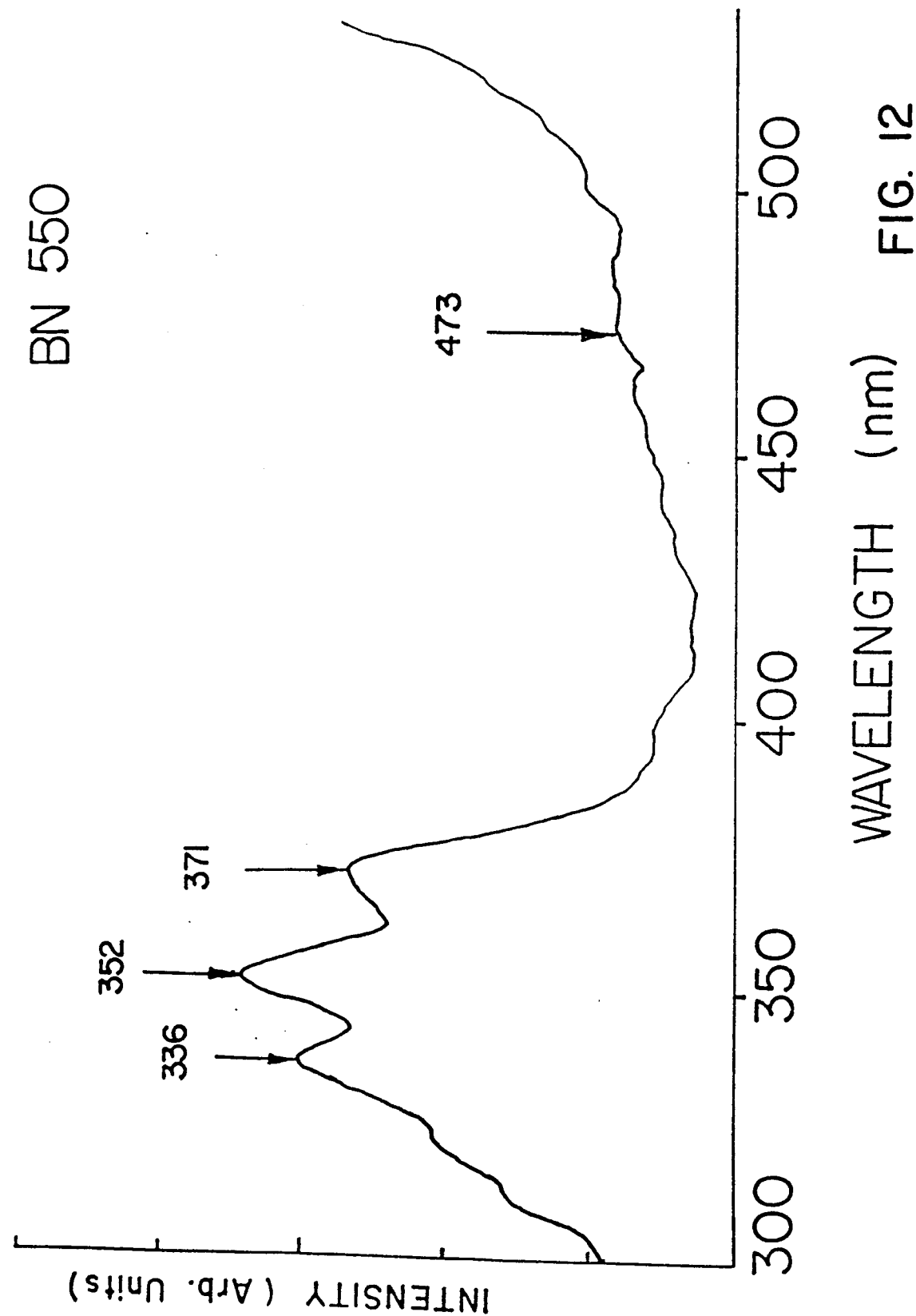
FIGS. 12 and 13 are typical excitation spectra measured at 550 nm from native human breast normal tissue times and native human breast tumor tissue.
Figure 13:
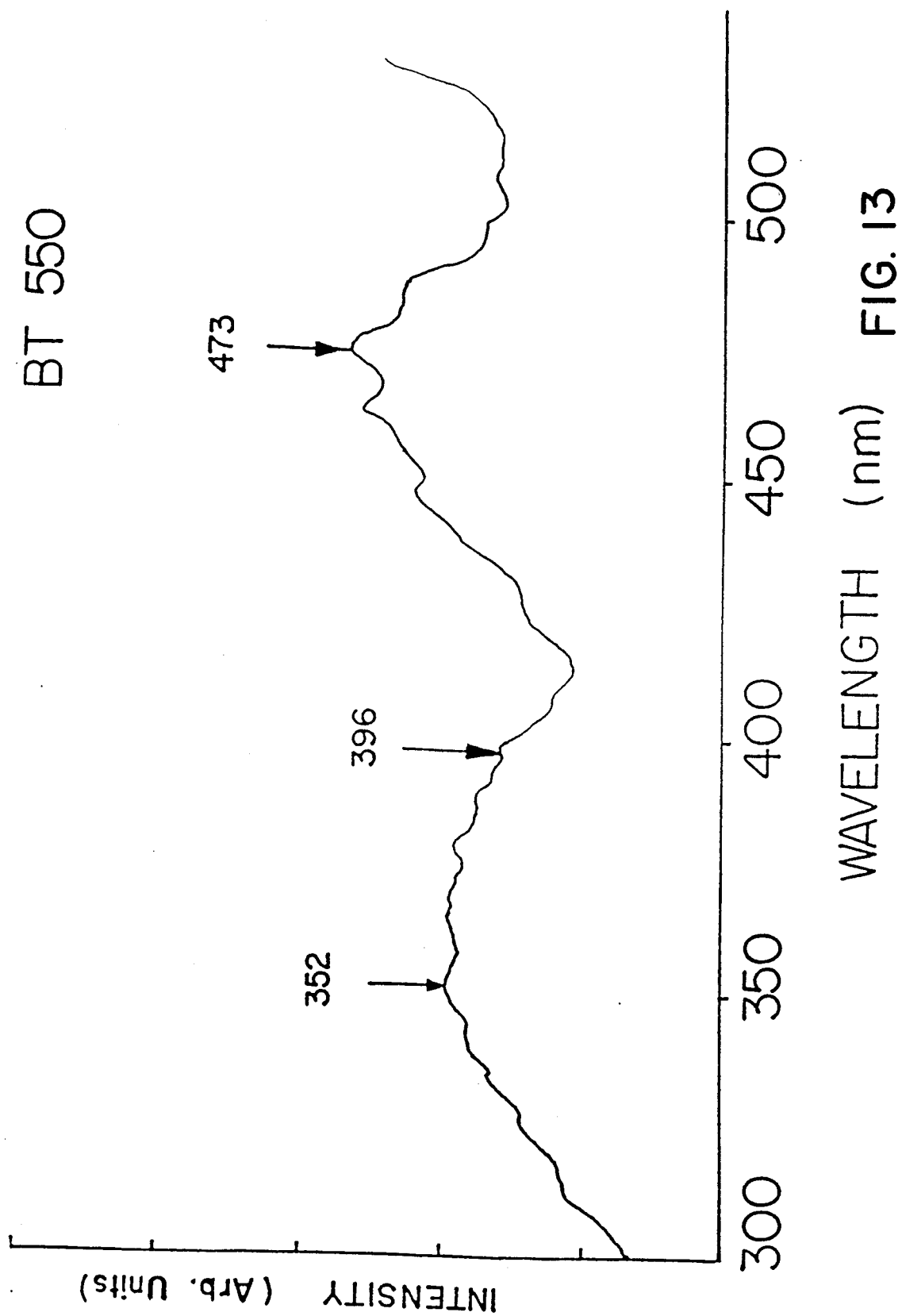

The main peak in the visible band of the excitation spectra in FIG. 10 and FIG. 12 for normal tissues is located at 473 nm. The intensities of the visible band are about four times weaker than the uv bands. However, for the tumor breast tissues in FIG. 11 and FIG. 13, the intensities of the visible bands are higher than the uv bands.

Figure 14:
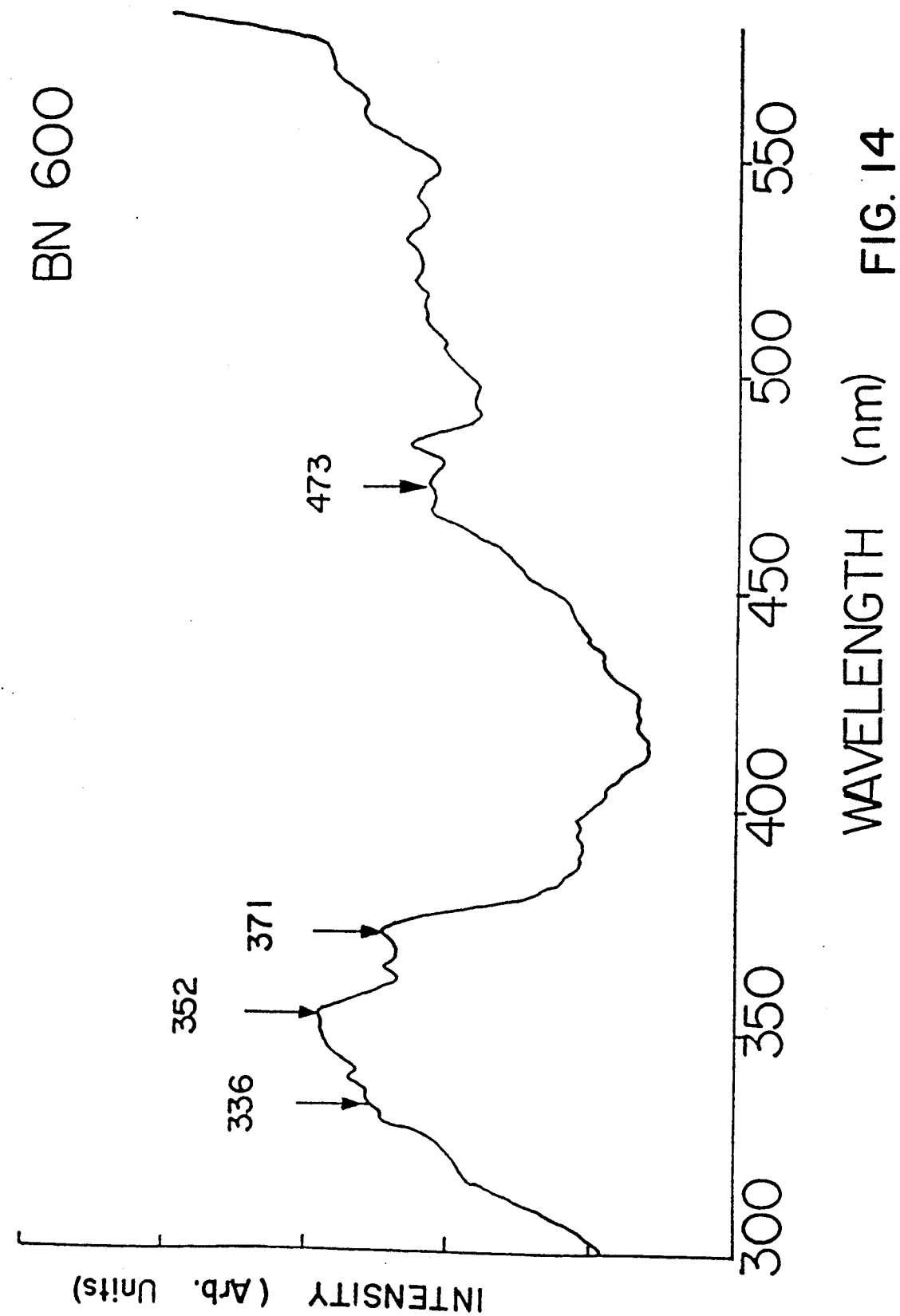
FIGS. 14 and 15 are typical excitation spectra measured at 600 nm from native human breast normal tissue and native human breast tumor tissue respectively.
Figure 15:
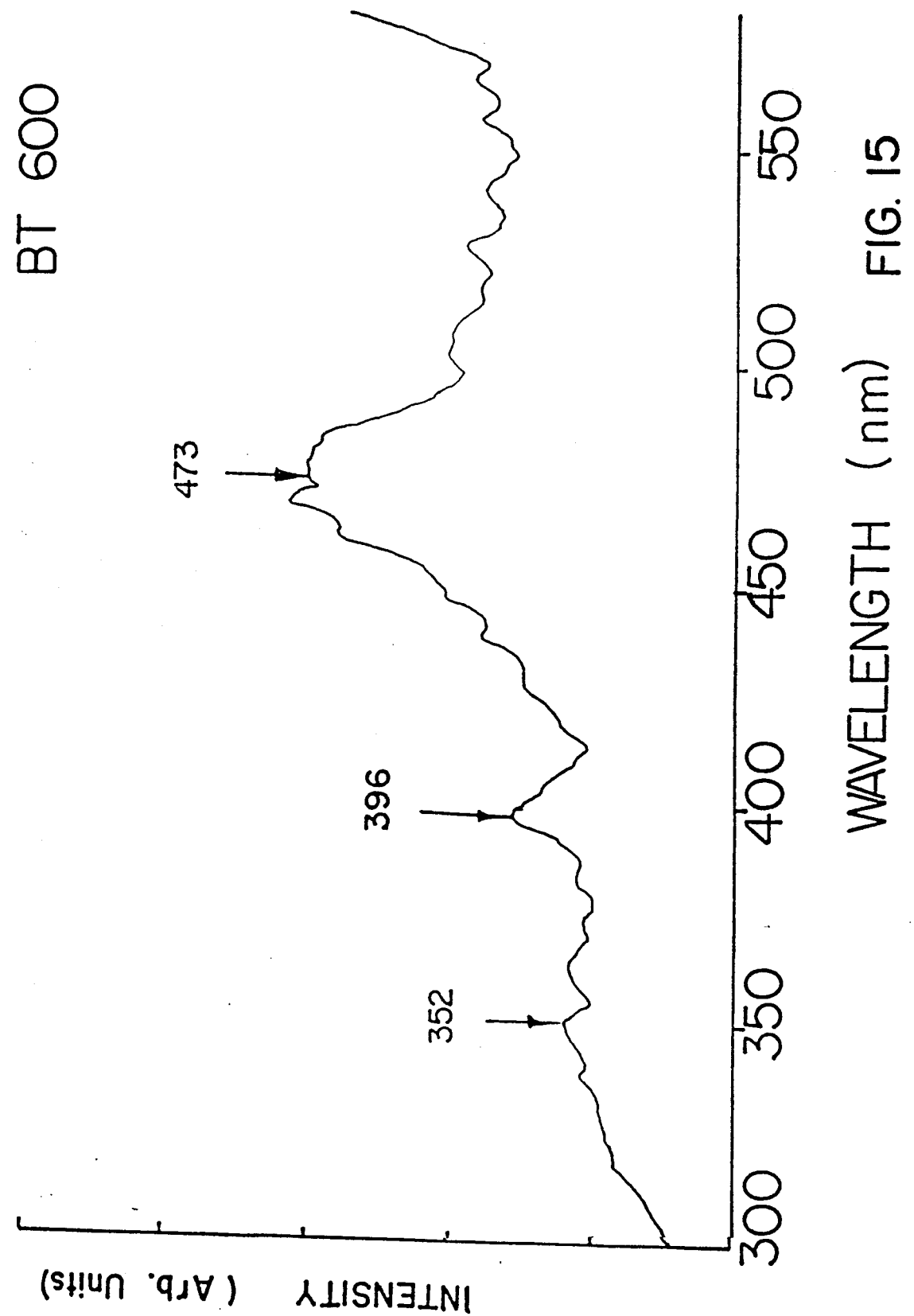

The excitation spectra for emission wavelength at 600 nm for normal and tumor tissues are shown in FIG. 14 and FIG. 15. The larger difference between the structures in the excitation spectra for normal and tumor tissues can be easily noticed. Structures exist in uv spectra for normal tissue while a broad band with a peak at 396 nm exists for cancer tissues. A visible band at 473 nm exists in both spectra. The intensity differences for the excitation spectra of tumor tissues from normal tissues are displayed in the table in FIG. 16 for emissions at 520 nm, 550 nm, and 600 nm. The ratios between the excitation intensities for tumor and normal tissues can serve as a diagnostic marker.

The excitation spectra in the uv band from normal tissues consist of three peaks while the tumor excitation spectra are without much distinct peaks. The uv band of the tumor excitation spectra are much wider than the uv band of the normal tissues due to the existence of the 396 nm peak. We should point out that the broad spectrum and the peak at 396 nm may be a characteristic of cancer in the excitation spectra which may be used to distinguish cancer from normal tissues. These differences suggest that the electronic states of fluorophores are altered in cancer cells in comparison to those molecules in the normal cells.

The visible bands of the excitation spectra show clear differences in the electronic band centered at 473 nm for the excitation spectra intensity. The intensity of the tumor tissue for 520 nm is 5.38 times larger at 457.9 nm and 2.59 times larger at 488 nm than for the normal tissues. The excitation spectrum intensity for 550 nm is 5.16 times stronger at 457.9 nm and 3.53 times stronger at 488 nm that that of the normal tissues. However, the differences are much weaker for uv. These results support the fact that the cancer fluorescence emission spectra are different and stronger than normal tissue spectra for 488 nm excitation and only slightly different for uv excitation. Thus, excitation spectroscopy can be used as a diagnostic tool for the detection of pathological changes in tissues.

In the FIG. 6 embodiment the fiber optic bundle could be replaced by a microscope for microscopic analysis of normal and cancerous tissue. Also in FIG. 9 the photodetector 215 could be replaced by a video system.

The embodiments of the present invention is intended to be merely exemplary and those skilled in the art shall be able to make numerous variations and modifications to it without departing from the spirit of the present invention. All such variations and modifications are intended to be within the scope of the present invention as defined in the appended claims.

What is claimed is:

1. Apparatus for detecting cancerous tissue comprising:
   a. means for illuminating a sample tissue with a beam of monochromatic light,
   b. means for varying the wavelength of said beam of monochromatic light,
   c. means for detecting emitted light from the sample at a predetermined wavelength as said wavelength of monochromatic light is varied, thereby obtaining an excitation spectral profile, and d. means for comparing the spectral profile so obtained with a spectral profile obtained in the same manner of a normal tissue, or cancerous tissue or cancerous tissue and normal tissue.

2. The apparatus of claim 1 and wherein the illuminating means comprises a light source and a spectrometer.

3. The apparatus of claim 1 and wherein the detecting means comprises a spectrometer and a photomultiplier.

4. The apparatus of claim 1 and wherein the comparing means comprises a computer.

5. The apparatus of claim 1 and further including an endoscope coupled to said illuminating means for directing said beam of light to said sample.

6. A method of determining if a sample tissue is cancerous comprising:
a. illuminating said sample tissue with a beam of monochromatic light having a changing wavelength,
b. detecting emitted light from the sample tissue at a predetermined emission wavelength, obtaining thereby an excitation spectral profile
c. comparing said excitation spectral profile with an excitation spectral profile obtained in the same manner at said same predetermined emission wavelength for a normal tissue or for a cancerous tissue or for cancerous tissue and for normal tissue.

* * * * *